United States Patent [19]

Frank et al.

[11] Patent Number: 4,677,208
[45] Date of Patent: Jun. 30, 1987

[54] MANUFACTURE OF OXAZOLIDINES BY THE ALKOXYLATION OF IMINES

[75] Inventors: Dieter Frank, Naperville; Hee Cho, Westmont, both of Ill.

[73] Assignee: Akzona Incorporated, New York, N.Y.

[21] Appl. No.: 765,053

[22] Filed: Aug. 12, 1985

[51] Int. Cl.[4] ............................................. C07D 263/04
[52] U.S. Cl. .................................................... 548/215
[58] Field of Search ......................................... 548/215

[56] References Cited

U.S. PATENT DOCUMENTS 3,743,626  7/1973  Emmons ............................. 528/73
3,897,362  7/1975  McCoy ............................... 564/278
3,912,691  10/1975  Emmons ............................ 548/216

OTHER PUBLICATIONS

Fokin et al, Izvestiya Akademii Nauk SSSR Seriya Kimicheskaya, vol. 8, 1982, pp. 1872–1876.
Fokin et al, Chem. Abst. 98-4493j.

Primary Examiner—Donald G. Daus
Assistant Examiner—Cecilia Shen
Attorney, Agent, or Firm—Louis A. Morris; Francis W. Young

[57] ABSTRACT

N-substituted mono or bis-oxazolidines may be manufactured by reacting an alkylene oxide at alkoxylating conditions with a mono-imine of the general formula:

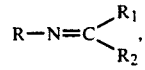

or a bis-imine of the general formula:

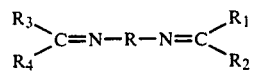

wherein R is a linear or branched alkyl, aryl, aralkyl, alkylenyl or aryllenyl group having 1–22 carbon atoms, and $R_1$, $R_2$, $R_3$ and $R_4$ may be the same or different, and are selected from the group including H—, methyl, ethyl, isobutyl, isoamyl, or phenyl. The oxazolidine may thereafter be cleaved with water, preferably slightly acidified, to produce the monoethoxylated amine.

10 Claims, No Drawings

MANUFACTURE OF OXAZOLIDINES BY THE ALKOXYLATION OF IMINES

BACKGROUND OF THE INVENTION

This invention is directed to a method for the manufacture of N-substituted-oxazolidines. More specifically, the invention is directed to a method for their manufacture using substituted imines. Oxazolidines are useful as intermediates in the production of monoalkoxylated amines.

Processes for the manufacture of compounds similar to the oxazolidine of the present reaction from imines and substituted oxiranes are disclosed in Chemical Abstracts, Vol. 98, 4493j, an abstract of the article in Izvestiya Akademii Nauk SSSR Seriya Kimicheskaya, v. 8, pp. 1872-1876 (1982), entitled "[2+3] Cycloadditions of Oxiranes and Thiiranes." The authors, A. V. Fokin, A. F. Kolomiets, G. F. Illin, and T. J. Fedyushina, disclose that oxiranes undergo cycloaddition with $RSO_2N{:}CR_1CF_3$ in the manner as shown in the following example:

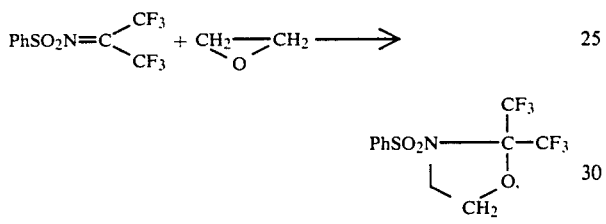

As may be seen by the product's formula, the substitution at the nitrogen atom of the oxazolidine includes an $—SO_2$-group. This reference teaches that the imine of hexafluoroacetone (no substituted $—SO_2—$ on the nitrogen) will not react with ethylene oxide under mild conditions.

U.S. Pat. No. 3,743,626 to Emmons (Emmons I) teaches preparation of oxazolidine intermediates by several different methods. In one method, a Michael addition product, such as that formed by reacting a primary alkanolamine with an ester of $\alpha,\beta$-ethylenically unsaturated carboxylic acid, is reacted with an appropriate carbonyl compound to produce a monofunctional oxazolidine having ester functionality. In another method an aldehyde is reacted with ethanolamine to form a reaction mixture containing oxazolidine. The oxazolidine having ester functionality as above prepared is then transesterified by reaction with an unsaturated polyol, such as polyoxyalkylene polyol prepared by the addition of ethylene oxide to water.

U.S. Pat. No. 3,897,362 to McCoy describes the preparation of alkoxylated Schiff bases. First, a monoethoxylated Schiff base is made e.g., from aminoethanol and ketone. Ethylene oxide is then catalytically reacted with the Schiff base to form linear polyethoxylates, i.e. the ethylenoxide adds to the hydroxyl group.

U.S. Pat. No. 3,912,691, Emmons (Emmons II), discloses at column 6, lines 16-41, the cleaving with water (hydrolysis) of an oxazolidine to form a monoethoxylated amine. Trace amounts of moisture in the atmosphere are sufficient to initiate this hydrolysis. Emmons II incorporates Emmons I by reference in describing the preparation of the oxazolidines.

Other prior art discloses the manufacture of N-alkyl monoethoxylated amines by the direct addition of an N-alkyl amine to ethylene oxide. However, this process results in a conversion to the desired product of only about 25%, with 50% being converted to a diethoxylated amine and 25% remaining as unreacted amine. In addition to these low yields, a further problem arises in that the resulting mixture cannot be readily distilled or otherwise separated into its component parts.

Another prior art method comprises blending a primary amine with chlorohydrin to form an N-alkyl monoethoxylated ammonium chloride, which is thereafter neutralized with sodium hydroxide to form the N-alkyl monoethoxylated amine. The high cost of chlorohydrin renders this method somewhat undesirable.

Long chain N-alkyl monoethoxylated amines may also be manufactured by adding long-chain N-alkyl aldehydes to a alkanolamine, but the high cost of such aldehydes renders such a process commercially uneconomical.

SUMMARY OF THE INVENTION

The primary objective of the present invention is to provide a method for the manufacture of an N-substituted mono or bis-oxazolidine as an intermediate product which is particularly useful in the production of monoethoxylated amines.

Accordingly, the invention is a method for the manufacture of an N-substituted-oxazolidine, comprising reacting an alkylene oxide at alkoxylating conditions with a mono-imine of the general formula:

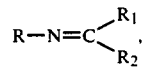

or a bis-imine of the general formula:

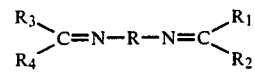

wherein R is a linear or branched alkyl, or cycloalkyl, aryl, aralkyl, alkylenyl, or aryllenyl group having 1-22 carbon atoms, $R_1$, $R_2$, $R_3$ and $R_4$ may be the same or different and are selected from the group hydrogen, methyl, ethyl, isobutyl, isoamyl, or phenyl. The oxazolidine product will be N-substituted mono or bis where the starting imine is mono or bis, respectively.

Other embodiments of the present invention emcompass details about substituted alkyl groups on the imine and alkylene oxide reactants, alkoxylating conditions and the obtaining of monoalkoxylated amines from the oxazolidine intermediates.

DESCRIPTION OF THE PREFERRED EMBODIMENTS

The general procedure for the manufacture of the present N-substituted-oxazolidines may be described as follows. First, an imine should be either obtained or may be prepared, for example, by reacting an aliphatic amine with a ketone, and distilling off any volatiles formed. Then, the imine is placed in a reactor and an alkylene oxide is added in stoichiometric or greater amounts. The alkoxylation will preferably take place at between about 140° and about 250° C., the most preferred alkoxylation temperature being 200° C. Alkylene oxide is added at a rate so as to maintain the reactor at a preferred pressure between about 40 and about 50 psig, although the initial pressure prior to commencing the reaction may be somewhat lower. Higher pressures may be used to hasten the reaction, but are considered unsafe. Generally, the alkoxylation will take between 3 and 24 hours, the former time being typical of alkoxylation when the pressure during alkoxylation is maintained significantly above the preferred 40 to 50 psig. After alkoxylation is completed, the reaction mixture may be distilled and/or evaporated so as to obtain a pure oxazolidine in quantities typically approaching 78% of the theoretical yield. Evaporation is typically done under reduced pressure, and distillation is commonly done at either atmospheric pressure or at a reduced pressure of between 0.2 mm Hg and 0.5 mm Hg.

The purified oxazolidine may then be cleaved with water or preferably acidic water to form a crude monoalkoxylated amine. Typical molar ratios of water to oxazolidine are from about 1:1 to about 11:1. A ratio of 1:1 is the theoretical lower limit and would suffice, although the reaction would go to completion very slowly. The crude monoalkoxylated amine is then distilled to remove any remaining ketone, amine, imine, and water at temperatures suitable to the particular amine and at reduced pressures, typically less than 1.0 mm Hg. The monoalkoxylated amine may then be separated and dried under vacuum with stirring at about 80° C., and an optional final distillation step under vacuum may be performed at suitable temperatures and pressures less than 1 mm Hg. The water may be acidified with an acid such as hydrochloric, acetic, sulfuric, various Lewis acids such as $BF_3$, $AlCl_3$ and other organic acids such as carboxylic or sulfonic. The amount of acid that might be used is catalytic, i.e. up to about 1 equivalent of acid per 10 equivalents of oxazolidine.

The linear or branched chain alkyl group, cycloalkyl, aryl, aralkyl, alkylenyl or aryllenyl group having 1 to 22 carbon atoms attached to the nitrogen of the imine reactant (or nitrogens in the case of a bis-imine reactant) may preferably be one of the radicals; dodecyl, ethyl, tallow alkyl, coco alkyl, oleyl alkyl or methyl or hydrogenated tallow alkyl. The alkylene oxide reactant is most likely to be ethylene oxide, but could also be propylene oxide or any substituted alkylene oxide capable of reacting with the imine double bond to form an oxazolidine.

The accomplishment of the method of the present invention is surprising and unexpected in view of the teaching of the above Fokin et al article. Fokin et al shows a requirement for the substituents on an imine to be electron withdrawing for reaction with ethylene oxide to be enabled. The sulfonyl and halogenated substituents are electron deficient, thus having the following schematic effect:

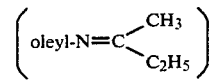

In fact, Fokin et al teaches that where the structure lacks the sulfonyl group, such as with the imine of hexafluoroacetone, a reaction with ethylene oxide under mild conditions will not be achieved. Fokin et al does not define what is meant by "mild conditions", but even assuming that Fokin et al teaches that the imine of hexafluoroacetone could be ethoxylated at relatively severe conditions, such teaching would still include the requirement of at least two electron withdrawing substituents, i.e. the halogenated groups, and that the reaction would always require, at least to some degree, withdrawal of electrons from the imine nitrogen to carbon double bond. The teaching of Fokin et al would, therefore, lead one to believe that the Fokin et al method could never produce an N-substituted-oxazolidine from an imine having no electron withdrawing substituent.

In contradistinction to Fokin et al the present invention requires the imine reactant to have all three substituents comprising electron donating groups, thus having the following schematic effect (shown as a mono-imine for simplicity):

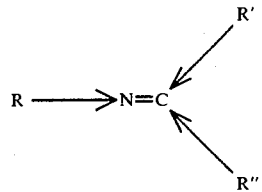

In the method of the present invention there is an electron rich double bond reacting with the alkylene oxide which is completely unexpected in view of the teaching of Fokin et al that an electron deficient double bond is required.

With further regard to the above discussed patent to McCoy, the ethylene oxide, when reacting with the Schiff base as shown in that reference, will add to the hydroxyl group to form a polyethoxylate. In contradistinction thereto, in the method of the present invention ethylene oxide addds to the imine double bond.

The following non-limiting examples demonstrate preferred embodiments for practice of the present invention.

EXAMPLE 1

Eight hundred grams (2.5 grams moles) of N-oleyl ($C_{18}H_{35}$—) methyl ethyl ketimine

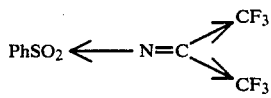

were placed in a two-liter autoclave which was then purged with five successive nitrogen charges, with the reactor vented to near atmospheric pressure after each charge. The contents were heated to 200° C., and the reactor pressure at that time was approximately 10 psig. Approximately 3.0 gram moles of ethylene oxide (a 20% excess) were added at a rate so as to maintain the reactor pressure between 40 and 50 psig. At the end of fifteen hours, the reaction had gone to completion as indicated by the nearly complete consumption of the ethylene oxide and by the almost total reduction of the imine absorption band (1670 cm$^{-1}$), from the chart produced upon infrared analysis of the reaction mixture. The mixture was evaporated under a reduced pressure to yield 923 grams of the crude oxazolidine in the form of a brownish liquid. 570 grams of this liquid was distilled, with a first 17 gram fraction removed at 180° C. and 0.2 mm Hg and discarded. The 435 grams removed at 185° C. and 0.2 mm Hg and at 205° C. and 0.5 mm Hg was a pale yellow liquid comprising substantially pure N-oleyl-oxazolidine having the formula:

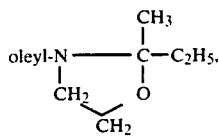

The yield was 78%, based upon the amount of N-oleyl imine used. A typical oleylamine that may be used in the manufacture of the present imines will comprise approximately 95% of the primary amine ($C_{18}H_{35}NH_2$) and 5% secondary amine.

Four hundred and fifteen grams (415 grams, 1.16 gram moles) of this N-oleyl-oxazolidine and 209 grams (11.6 grams moles) water were heated with stirring in a flask equipped with a distilling condenser. The distillation proceded over the next five hours, with the pot temperature maintained at about 110°–130° c., and the distillate comprised approximately 90 ml of an upper layer of methyl ethyl ketone and a lower layer having an undetermined volume and comprising water.

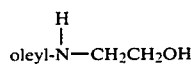

was formed, which solidified on standing. The product was made according to the following reaction:

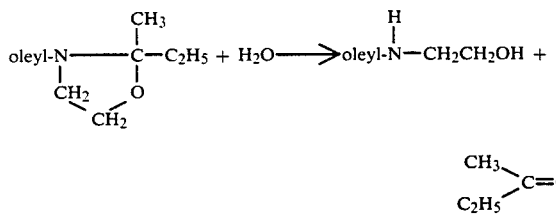

EXAMPLE 2

Five hundred and fifty-two grams (1.75 grams moles) of N-tallow methyl ethyl ketimine

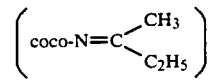

was placed in a two-liter autoclave, which had been purged with five successive nitrogen charges with venting of the reactor to near atmospheric pressure after each charge. The contents were heated to 200° C., and the reactor pressure at that time was approximately 10 psig. Approximately 2.1 gram moles of ethylene oxide (a 20% excess) were added at a rate so as to maintain the reactor pressure between 40 and 50 psig. At the end of fifteen hours, the reaction had gone to completion as indicated by the nearly completely digestion of the ethylene oxide and by the almost total reduction of the imine absorption band (1670 cm$^{-1}$) from the chart produced upon infrared analysis of the reaction mixture. The mixture was evaporated under a reduced pressure to yield 603 grams of the crude N-tallow-oxazolidine in the form of a brown liquid.

All of this crude N-tallow-oxazolidine and 315 grams (17.5 gram moles) water were heated with stirring in a flask equipped with a distilling condenser. The distillation proceeded over the next five hours, with the pot temperature maintained at about 100°–130° C., and the distillate largely comprising methyl ethyl ketone.

The product in the still pot was separated and dried under a vacuum at about 80° C. with stirring. It was then distilled under vacuum (120°–200° C. at 0.3 mm Hg) to give 272 grams (61% theoretical yield) of N-tallow-monoethoxylated amine:

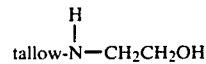

which solidified to an off-white color on standing. The product was made according to the following reaction:

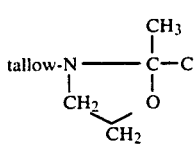

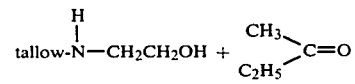

EXAMPLE 3

Nine hundred and three and seven-tenths grams (3.57 gram moles) of N-coco methyl ethyl ketimine

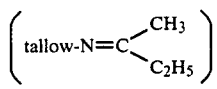

was placed in a two-liter autoclave, which had been purged with five successive nitrogen charges with venting of the reactor to near atmospheric pressure after each charge. The contents were heated to 200° C., and the reactor pressure at that time was approximately 10 psig. Approximately 4.3 gram moles of ethylene oxide (a 20% excess) were added at a rate so as to maintain the reactor pressure between 40 and 50 psig. After twenty-four hours, the reaction had gone to completion as indicated by the nearly complete digestion of the ethylene oxide and by the almost total reduction of the imine absorption band (1670 cm$^{-1}$) from the chart produced upon infrared analysis of the reaction mixture. The mixture was evaporated under a reduced pressure to yield 1082 grams of the crude N-coco-oxazolidine in the form of a brownish liquid. Vacuum distillation (180° C.–205° C. at 0.5 mm Hg) of the crude product yielded a substantially pure N-coco-oxazolidine in an amount corresponding to 78% of the theoretical.

Five hundred and thirty-eight grams (538 grams, 1.83 gram moles) of this N-coco-oxazolidine and 329 grams (18.3 gram moles) water were heated with stirring in a flask equipped with a distilling condenser. The distillation proceded over the next five hours, with the pot temperature maintained at about 110°–130° C., and the distillate formed was methyl ethyl ketone.

The product in the still pot was separated and dried under a vacuum at about 80° C. Four hundred and thirty-nine (439) grams of a brownish liquid, N-coco-monoethoxylated amine:

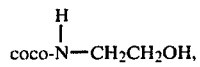

was formed. The product was made according to the following reaction:

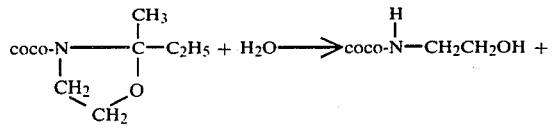

EXAMPLE 4

One hundred and sixteen grams (1.16 gram moles) of N-ethyl methyl ethyl ketimine

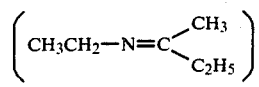

was placed in a two-liter autoclave which had been purged with three successive nitrogen charges, with the reactor vented to near atmospheric pressure after each charge. The contents were heated to 160° C. An equimolar amount (1.16 gram moles) of ethylene oxide was added to the reactor, the pressure therein now exceeding 200 psig. However, the reaction between the ethylene oxide and the ketimine did not begin until the temperature was increased to 180° C. Some additional ethylene oxide was added, lowering the temperature of the reaction mix. At the end of five hours, the reaction had gone to completion as indicated by the complete digestion of the ethylene oxide. The mixture was distilled at atmospheric pressure to yield 93 grams of colorless liquid comprising substantially pure N-ethyl oxazolidine:

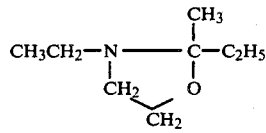

Seventy-one and one-half grams (71.5 grams, 0.5 gram moles) of this N-ethyl-oxazolidine, 27 grams (1.5 gram moles) of water, and one drop of concentrated hydrochloric acid were heated with stirring in a flask equipped with a distilling condenser. Two layers formed which dissipated into one upon heating to 50° C. The distillation proceded over the next several hours, with the head temperature maintained at about 166.5°–167.5° C., and 42 grams of the distillate was collected.

The product in the still pot was separated and dried under vacuum in a rotary evaporator. Thirty-nine (39) grams of an N-ethyl monoethoxylated amine:

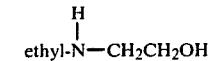

was formed. The product was made according to the following reaction:

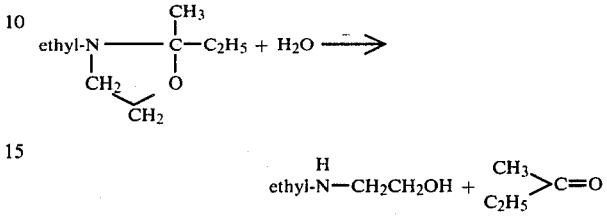

EXAMPLE 5

An imine was prepared by blending 2200 ml (approximately 1750 grams) of Armeen ®O aliphatic amine and 1273 ml (1.5 equivalents) of methyl isoamylketone in a five-liter, four-neck round-bottom flask. Armeen ®O aliphatic amine is Akzo Chemie America's trademark for oleylamine ($C_{18}H_{35}NH_2$) comprised of approximately 95.0 primary amine and 5.0% secondary amine. The flask included a heating mantle and was topped off with a 60 cm Vigreaux column with a heated jacket, water trap, and condenser. The amine/ketone blend was heated until the azeotrope was evolved into the trap. When 25 ml of water accumulated in the trap, the flask contents were at 110° C. and water removal was commenced.

The distillation was continued for six hours and at the end of that time, the flask temperature was 155° C. To prevent severe bumping during the distillation, 200 ml benzene was added and an additional 39 ml of water was taken off the system while under nitrogen atmosphere. Then, additional volatiles, primarily benzene, water, and ketone, were removed from the system while under vacuum. The product remaining was N-oleylmethylisoamyl ketimine:

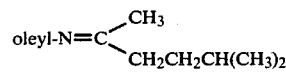

All 2540 grams of this product in the flask above and the approximately 10% unreacted ketone therein was placed in a two-gallon reactor. The system was purged and then pressurized with nitrogen to the required 8–10 psig at the preferred reaction temperature of 185° C.–200° C. Ethylene oxide was then introduced as needed in accordance with standard ethoxylation procedures. The reaction was continued over the course of three eight-hour day shifts, with the ethylene oxide and the heat to the reactor stopped between shifts. After a total reaction time of approximately twenty-four hours, the reaction was essentially completed in that no imine band appeared upon infrared analysis of a sample of the reactor contents. The product formed was 3-oleyl-2-methyl-2-(isoamyl-oxazolidine in accordance with the reaction:

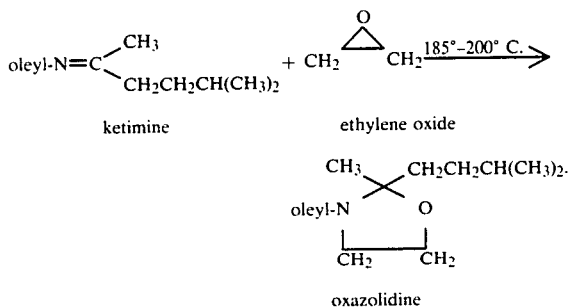

ketimine    ethylene oxide

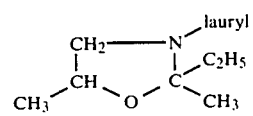

oxazolidine

This oxazolidine was cleaved with acidic water by adding approximately one liter of the oxazolidine to a two-liter, three-necked round bottom flask with a thermometer and stillhead U-tube attached. The system was heated and 450 ml of water and 2 ml of glacial acetic acid were added thereto. The ketone remaining in the oxazolidine and the water were removed as rapidly as necessary to maintain smooth reflux. The reaction was continued until the near absence of the carbon-oxygen double bond (indicating an absence of ketone through its removal with the condensate) was noted on the infrared chart of a sample of the flask's contents. NMR analysis indicated the presence of small amounts of oxazolidine, primary amine, and ketone, but no imine was noted.

The oleyl ethoxylated amine was formed according to the reaction:

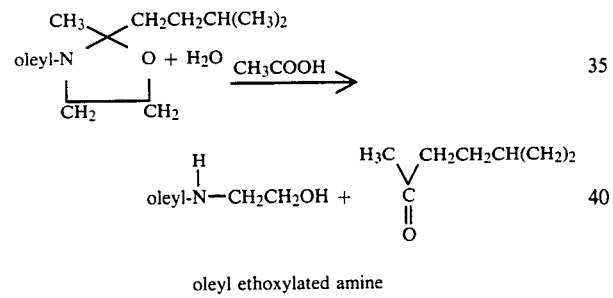

oleyl ethoxylated amine and all 617.6 grams of the crude product formed was placed in a two-liter distillation flask having a distilling column (20 cm Vigreaux) and a condenser. The system was heated and placed under a vacuum of less than 1.0 mm Hg, and the forerun contained some ketone, amine, imine, and water. 295 grams of the product, a yellowish liquid whose sample upon IR analysis showed only a trace of carbonyl bond, was distilled off the column at approximately 200° C. and 0.5 mg Hg. The pot's residue of approximately 400 milliliters was further distilled to give 75.1 additional grams of product that was removed at 228° C. and 6.2 mm Hg. The monoethoxylated amine solidified upon standing at room temperature.

EXAMPLE 6

2,5-dimethyl-2-ethyl-3-lauryloxazolidine

N-lauryl-2-butanimine (65 g) was charged to a 450 ml autoclave which was then purged four times with nitrogen. After heating to 200° C. the pressure was lowered to 5 psig, then propylene oxide was added to 50–60 psig. After 20 hours, the addition of propylene oxide to the imine was complete as indicated by the absence of the IR imine absorption bond. Vacuum distillation of the product mixture gave 2,5-dimethyl-2-ethyl-3-lauryloxazolidine (34 g, 42%) represented by the following formula:

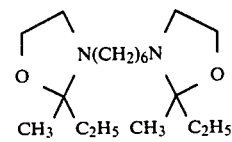

N-(2-hydroxypropyl)laurylamine

A mixture of 2,5-dimethyl-2-ethyl-3-lauryloxazolidine (10 g) and water (20 g) was heated at reflux for six hours. After evaporation of the volatile components and drying, N-(2-hydroxypropyl)laurylamine was obtained in quantitative yield.

EXAMPLE 7

Following the procedure developed for monoamines, a bis-imine was prepared from 144 g 1,6-hexanediamine and 192 g 2-butanone with 100 ml of toluene as the azeotropic agent. After removal of the volatile components under vacuum, the bis-imine was reacted with ethylene oxide at 195°–205° C. and 50 psig of ethylene oxide. After seven hours re-reaction time the C=N stretching band was absent in the infrared spectrum of the reaction product. This product was removed from the autoclave then subjected to bulb-to-bulb distillation at 180° C. under high vacuum for five hours to give 141.7 g distillate and 79.9 g bottoms. NMR analysis of the distillate indicated a predominance of the desired bis-oxazolidine.

EXAMPLE 8

From 819 g 4,4'-methylenebis(cyclohexylamine) and 750 ml of 2-butanone using 150 ml benzene as the azeotropic agent, a bis-imine was prepared in essentially quantitative yield. Of this, 675 g was subjected to ethoxylation conditions (195°–205° C., ethylene oxide to 50 psig). After the imine had been consumed, as indicated by IR analysis, 815 g of a viscous amber liquid containing predominantly the desired bis-oxazolidine was obtained. The bis-oxazolidine was hydrolyzed using an excess of water and a catalytic amount of HCl. Continuous and complete removal of 2-butanone afforded the desired bis-monoethoxylated amine.

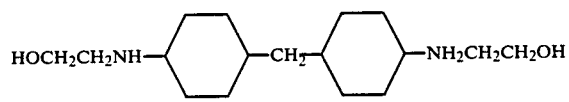

What is claimed is:

1. A method for the manufacture of an N-substituted mono or bis-oxazolidine comprising reacting an alkylene oxide at a temperature from about 40° C. to 250° C., a pressure less than about 50 psig and a reaction time of from about 2 hours to about 25 hours with a mono-imine of the formula:

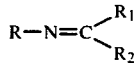

or a bis-imine of the formula:

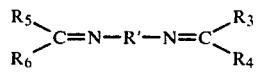

wherein R is a linear or branched chain alkyl group having 2 to 22 carbon atoms, R' is a linear or branched chain alkyl group having 2 to 22 carbon atoms or a group of the formula

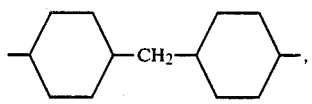

$R_1$ and $R_2$ may be the same or different and are selected from the group consisting of hydrogen, methyl, ethyl, isobutyl, isoamyl, and phenyl and $R_3$, $R_4$, $R_5$, and $R_6$ may be the same or different and are selected from the group consisting of methyl, ethyl, isobutyl, isoamyl, and phenyl to form said oxazolidine.

2. The method of claim 1, wherein the amount of alkylene oxide reacted with the imine is stoichiometric or greater.

3. The method of claim 1, wherein the alkylene oxide is ethylene oxide, or propylene oxide.

4. The method of claim 1, wherein R or R' is selected from the group comprising the dodecyl radical, ethyl radical, tallow alkyl radical, coco alkyl radical, or oleyl alkyl radical.

5. The method of claim 4, wherein said imine is a mono-imine, R is the oleyl alkyl radical, $R_1$ is methyl, and $R_2$ is ethyl.

6. The method of claim 4, wherein said imine is a mono-imine, and R is the tallow alkyl radical.

7. The method of claim 4, wherein said imine is a mono-imine, and R is the coco alkyl radical.

8. The method of claim 4, wherein said imine is a mono-imine, and R is the ethyl radical.

9. The method of claim 1, wherein after being formed, said oxazolidine is cleaved by reacting with water to form a monoalkoxylated amine.

10. The method of claim 9, wherein the cleaving reaction is effected in the presence of an acid.

* * * * *